US00PP24286P2

(12) United States Plant Patent
Yamaguchi

(10) Patent No.: US PP24,286 P2
(45) Date of Patent: Mar. 4, 2014

(54) ***BEGONIA* PLANT NAMED 'SUNJIRADARE'**

(50) Latin Name: *Begonia×tuberhybrida*
Varietal Denomination: Sunjiradare

(75) Inventor: Hideki Yamaguchi, Narusawa-mura (JP)

(73) Assignee: Suntory Flowers Ltd., Tokyo (JP)

( * ) Notice: Subject to any disclaimer, the term of this patent is extended or adjusted under 35 U.S.C. 154(b) by 143 days.

(21) Appl. No.: 13/385,536

(22) Filed: Feb. 23, 2012

(51) Int. Cl.
*A01H 5/00* (2006.01)

(52) U.S. Cl.
USPC ..... Plt./349

(58) Field of Classification Search
USPC ..... Plt./349, 347
See application file for complete search history.

*Primary Examiner* — June Hwu
(74) *Attorney, Agent, or Firm* — C. A. Whealy

(57) ABSTRACT

A new and distinct cultivar of *Begonia* plant named 'Sunjiradare', characterized by its compact, outwardly spreading and mounding plant habit; vigorous growth habit; freely branching habit; and numerous single dark red-colored flowers that are held above and beyond the foliar plane.

1 Drawing Sheet

Botanical designation: *Begonia×tuberhybrida.*
Cultivar denomination: 'SUNJIRADARE'.

BACKGROUND OF THE INVENTION

The present invention relates to a new and distinct cultivar of *Begonia* plant, botanically known as *Begonia×tuberhybrida* and hereinafter referred to by the name 'Sunjiradare'.

The new *Begonia* plant is a product of a planned breeding program conducted by the Inventor in Narusawa-mura, Minamituru-gun, Yamanashi, Japan. The objective of the breeding program is to create new compact and freely branching *Begonia* plants with a mounding plant habit and attractive leaf and flower coloration.

The new *Begonia* plant originated from a cross-pollination made by the Inventor in Narusawa-mura, Minamituru-gun, Yamanashi, Japan in June, 2007 of a proprietary selection of *Begonia×tuberhybrida* identified as code number FC04Rp324N, not patented, as the female, or seed, parent with a proprietary selection of *Begonia×tuberhybrida* identified as code number FC04Cr312N2, not patented, as the male, or pollen, parent. The new *Begonia* plant was discovered and selected by the Inventor as a single flowering plant from within the progeny of the stated cross-pollination in a controlled environment in Narusawa-mura, Minamituru-gun, Yamanashi, Japan in July, 2008.

Asexual reproduction of the new *Begonia* plant by cuttings taken in a controlled greenhouse environment in Narusawa-mura, Minamituru-gun, Yamanashi, Japan since July, 2008 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunjiradare'. These characteristics in combination distinguish 'Sunjiradare' as a new and distinct *Begonia* plant:

1. Compact, outwardly spreading and mounding plant habit.
2. Vigorous growth habit.
3. Freely branching habit.
4. Numerous single dark red-colored flowers that are held above and beyond the foliar plane.

Plants of the new *Begonia* differ primarily from plants of the female parent selection in the following characteristics:

1. Plants of the new *Begonia* have thicker stems than plants of the female parent selection.
2. Plants of the new *Begonia* have smaller male flowers than plants of the female parent selection.
3. Plants of the new *Begonia* and the female parent selection differ in flower color as plants of the female parent selection have rose pink-colored flowers.

Plants of the new *Begonia* differ primarily from plants of the male parent selection in the following characteristics:

1. Plants of the new *Begonia* have larger leaves than plants of the male parent selection.
2. Plants of the new *Begonia* have larger male flowers than plants of the male parent selection.

Plants of the new *Begonia* can be compared to plants of *Begonia×tuberhybrida* 'Firecracker Orange', not patented. In side-by-side comparisons conducted in Narusawa-mura, Minamituru-gun, Yamanashi, Japan, plants of the new *Begonia* differed primarily from plants of 'Firecracker Orange' in the following characteristics:

1. Plants of the new *Begonia* were more compact than plants of 'Firecracker Orange'.
2. Plants of the new *Begonia* had shorter internodes than plants of 'Firecracker Orange'.
3. Plants of the new *Begonia* had shorter leaves and leaf petioles than plants of 'Firecracker Orange'.
4. Plants of the new *Begonia* and 'Firecracker Orange' differed in leaf and leaf petiole color.

5. Plants of the new *Begonia* had larger male flowers and smaller female flowers than plants of 'Firecracker Orange'.
6. Plants of the new *Begonia* and 'Firecracker Orange' differed in flower color as plants of 'Firecracker Orange' had orange red-colored flowers.
7. Plants of the new *Begonia* had shorter peduncles than plants of 'Firecracker Orange'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph at the top of the sheet comprises a side perspective view of a typical flowering plant of 'Sunjiradare' grown in a container.

The photograph at the bottom of the sheet is a close up view of a typical flower of 'Sunjiradare'.

DETAILED BOTANICAL DESCRIPTION

The aforementioned photographs and following observations and measurements describe plants grown during the autumn in 12-cm containers in a polyethylene-covered greenhouse in Higashiomi, Shiga, Japan under commercial practices. During the production of the plants, the day temperatures averaged 23° C. and the night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Begonia×tuberhybrida* 'Sunjiradare'.

Parentage:

*Female, or seed, parent.*—Proprietary selection of *Begonia×tuberhybrida* identified as code number FC04Rp324N, not patented.

*Male, or pollen, parent.*—Proprietary selection of *Begonia×tuberhybrida* identified as code number FC04Cr312N2, not patented.

Propagation:

*Type.*—By cuttings.

*Time to initiate roots, summer.*—About 15 days at temperatures of 17° C. to 28° C.

*Time to initiate roots, winter.*—About 15 days at temperatures of 14° C. to 23° C.

*Time to produce a rooted young plant, summer.*—About 40 days at temperatures of 17° C. to 28° C.

*Time to produce a rooted young plant, winter.*—About 40 days at temperatures of 14° C. to 23° C.

*Root description.*—Fine, fibrous; white in color.

*Rooting habit.*—Freely branching; plants of the new *Begonia* have been observed to form tubers during the winter.

Plant description:

*Plant form and growth habit.*—Compact and mounding plant habit, outwardly spreading; freely branching with good stem strength; flowers are single and positioned above and beyond the foliar plane; vigorous growth habit.

*Plant height.*—About 20.6 cm.

*Plant width.*—About 25.8 cm.

*Lateral branches.*—Length: About 18.9 cm. Diameter: About 5 mm. Internode length: About 2.6 cm. Aspect: Upright to outwardly. Texture: Sparsely pubescent. Color: Close to N199A tinted with close to 177A.

*Leaves.*—Arrangement: Alternate; simple. Length: About 10.4 cm. Width: About 4.2 cm. Shape: Lanceolate, asymmetrical. Apex: Acuminate. Base: Cordate. Margin: Serrate. Texture, upper and lower surfaces: Smooth, glabrous. Venation pattern: Palmate. Color: Developing and fully expanded leaves, upper surface: Close to N137A; venation, close to 138B. Developing and fully expanded leaves, lower surface: Close to 138B; venation, close to 138A tinted with close to 70C. Petioles: Length: About 2 cm. Diameter: About 2.8 mm. Texture, upper and lower surfaces: Sparsely pubescent. Color, upper and lower surfaces: Close to 177A. Stipules: Length: About 5.2 cm. Width: About 2.5 cm. Shape: Narrowly deltoid. Apex: Acute. Base: Truncate. Margin: Entire. Texture, upper and lower surfaces: Smooth, glabrous. Color, upper and lower surfaces: Close to 138C tinted with close to 184B.

Flower description:

*Flowering habit.*—Single flowers arranged in axillary cymes; usually about three to five flowers per cyme and about 13 cymes developing per plant; flowers positioned above and beyond the foliar plane; flowers not pendulous.

*Natural flowering season.*—Plants begin flowering about two months after planting; in the garden, plants flower continuously from the spring to late autumn in Japan; flowers not persistent.

*Fragrance.*—None detected.

*Male flowers buds.*—Length: About 2.3 cm. Diameter: About 9.3 mm. Shape: Ovoid. Color: Close to 46A.

*Male flowers.*—Shape: Cruciform. Diameter: About 4.7 cm. Depth (height): About 2.3 cm. Tepals: Quantity and arrangement: Four per flower in a single whorl. Length: About 2.9 cm. Width: About 1.3 cm. Shape: Lanceolate to ovate. Apex: Acute. Base: Obtuse. Margin: Entire. Texture, upper and lower surfaces: Smooth, glabrous. Color: When opening and fully opened, upper surface: Close to 46A. When opening and fully opened, lower surface: Close to 46A.

*Female flowers buds.*—Length: About 1.7 cm. Diameter: About 6.3 mm. Shape: Ovoid. Color: Close to 46A.

*Female flowers.*—Shape: Rounded. Diameter: About 4.1 cm. Depth (height): About 1.4 cm. Tepals: Quantity and arrangement: Five per flower in a single whorl. Length: About 2.2 cm. Width: About 5.9 mm. Shape: Lanceolate. Apex: Acute. Base: Obtuse. Margin: Entire. Texture, upper and lower surfaces: Smooth, glabrous. Color: When opening and fully opened, upper surface: Close to 46A. When opening and fully opened, lower surface: Close to 46A.

*Flower bracts.*—Length: About 6.7 mm. Width: About 7.2 mm. Color: Close to 180A.

*Peduncles.*—Angle: Outwardly. Length: About 3.4 cm. Diameter: About 1.5 mm. Texture: Smooth, glabrous. Color: Close to N144A tinted with close to 185A.

*Pedicels.*—Angle: Outwardly. Length: About 1.5 cm. Diameter: About 1 mm. Texture: Smooth, glabrous. Color: Close to N144A tinted with close to 185A.

*Reproductive organs.*—Stamens: Quantity: About 27 per male flower. Length: About 3.1 mm. Anther shape: Ovoid. Anther length: About 1.5 mm. Anther diameter: About 0.7 mm. Anther color: Close to 11A. Pollen amount: Moderate. Pollen color: Close to 11C.

*Pistils.*—Quantity: One per female flower. Length: About 9.2 mm. Stigma shape: Six-lobed, convoluted. Stigma color: Close to 25A and 17B. Style color: Close to 25A and 17B. Ovary length: About 7.1 mm. Ovary diameter: About 9.2 mm. Ovary color: Close to N34A and 144B.

*Seeds and fruits.*—Seed and fruit production have not been observed on plants of the new *Begonia.*

Postproduction longevity: Excellent postproduction longevity, plants last about 220 days.

Disease & pest resistance: Resistance to pathogens and pests common to *Begonias* has not been observed.

Temperature tolerance: Plants of the new *Begonia* have been observed to tolerate temperatures from about 14° C. to about 28° C.

It is claimed:

1. A new and distinct *Begonia* plant named 'Sunjiradare' as illustrated and described.

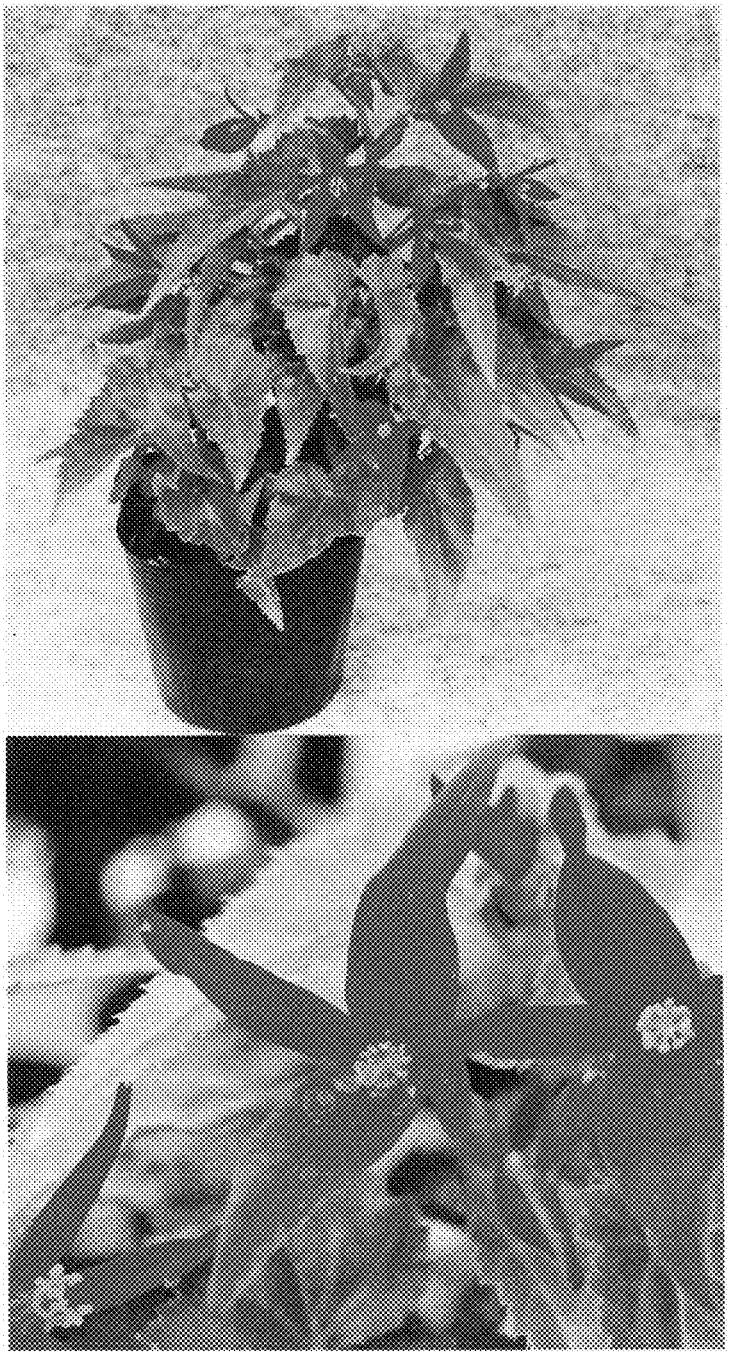

* * * * *